US008944996B2

(12) United States Patent
Saito (10) Patent No.: US 8,944,996 B2
(45) Date of Patent: Feb. 3, 2015

(54) ELECTRONIC ENDOSCOPE SYSTEM WITH OXYGEN SATURATION ENHANCING IMAGE REGION

(75) Inventor: Takaaki Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 386 days.

(21) Appl. No.: 13/015,872

(22) Filed: Jan. 28, 2011

(65) Prior Publication Data
US 2011/0237882 A1 Sep. 29, 2011

(30) Foreign Application Priority Data

Mar. 24, 2010 (JP) ................................. 2010-067453

(51) Int. Cl.
*A61B 1/04* (2006.01)
*A61B 5/1459* (2006.01)
(Continued)

(52) U.S. Cl.
CPC ............ *A61B 5/1459* (2013.01); *A61B 1/00009* (2013.01); *A61B 1/00045* (2013.01); *A61B 1/0005* (2013.01); *A61B 1/0638* (2013.01); *A61B 5/0084* (2013.01); *A61B 5/02007* (2013.01); *A61B 5/14551* (2013.01); *A61B 5/489* (2013.01); *G06T 7/0012* (2013.01); *H04N 5/2256* (2013.01); *A61B 5/7425* (2013.01); *A61B 1/063* (2013.01); *A61B 5/7485* (2013.01); *A61B 1/05* (2013.01); *G06T 2207/10024* (2013.01); *G06T 2207/10068* (2013.01); *G06T 2207/10152* (2013.01); *G06T 2207/30101* (2013.01); *H04N 2005/2255* (2013.01)
USPC ............................ 600/109; 600/160; 600/181

(58) Field of Classification Search
None
See application file for complete search history.

(56) References Cited

U.S. PATENT DOCUMENTS 4,878,113 A 10/1989 Nakamura
4,914,512 A * 4/1990 Sekiguchi ....................... 348/71
(Continued)

FOREIGN PATENT DOCUMENTS

| CN | 1725975 A | 1/2006 |
| EP | 2 305 094 A1 | 4/2011 |

(Continued)

OTHER PUBLICATIONS

Communication pursuant to Article 94(3) EPC issued in corresponding European Application No. 11152081.3 on Dec. 19, 2012.
(Continued)

*Primary Examiner* — Anhtuan T Nguyen
*Assistant Examiner* — Jae Woo
(74) *Attorney, Agent, or Firm* — Birch, Stewart, Kolasch & Birch, LLP (57) ABSTRACT

An electronic endoscope system includes a light source device for sequentially emitting plural kinds of light having different wavelength bands, an electronic endoscope for outputting image data of acquired images corresponding to the plural kinds of light sequentially illuminated to a subject tissue containing blood vessels, a setter for setting a blood vessel characteristics amount from the image data, a setter for setting a region of interest in the acquired image based on the amount, an image producer for producing a first oxygen saturation level image representing a distribution of an oxygen saturation level in the blood vessel from the image data, and an image display for displaying in simulated color a second oxygen saturation level image in which the oxygen saturation level within the region of interest is selectively enhanced.

9 Claims, 8 Drawing Sheets

(51) Int. Cl.

| | | |
|---|---|---|
| *A61B 1/00* | (2006.01) | |
| *A61B 1/06* | (2006.01) | |
| *A61B 5/00* | (2006.01) | |
| *A61B 5/02* | (2006.01) | |
| *A61B 5/1455* | (2006.01) | |
| *G06T 7/00* | (2006.01) | |
| *H04N 5/225* | (2006.01) | |
| *A61B 1/05* | (2006.01) | |

(56) References Cited

U.S. PATENT DOCUMENTS

| | | | | |
|---|---|---|---|---|
| 5,001,556 | A | * | 3/1991 | Nakamura et al. .............. 348/70 |
| 5,078,150 | A | * | 1/1992 | Hara et al. .................... 600/476 |
| 5,956,416 | A | * | 9/1999 | Tsuruoka et al. .............. 382/128 |
| 5,974,338 | A | * | 10/1999 | Asano et al. .................. 600/323 |
| 7,538,761 | B2 | | 5/2009 | Nishimura et al. |
| 7,539,335 | B2 | * | 5/2009 | Fukuyama .................... 382/128 |
| 7,912,534 | B2 | * | 3/2011 | Grinvald et al. .............. 600/476 |
| 8,090,177 | B2 | * | 1/2012 | Venkataraman et al. ..... 382/130 |
| 8,515,142 | B2 | | 8/2013 | Tsujita |
| 2009/0247881 | A1 | * | 10/2009 | Maeda et al. ................. 600/476 |
| 2010/0027863 | A1 | | 2/2010 | Venkataraman et al. |

FOREIGN PATENT DOCUMENTS

| | | |
|---|---|---|
| JP | 3-080834 A | 4/1991 |
| JP | 2660009 B2 | 10/1997 |
| JP | 2002-085342 A | 3/2002 |
| JP | 2004-188026 A | 7/2004 |
| JP | 2010-051350 A | 3/2010 |

OTHER PUBLICATIONS

Communication pursuant to Article 94(3) EPC issued in corresponding European Application No. 11152081.3 on Oct. 10, 2013.
Office Action issued in Chinese Application No. 201110035036.X on Dec. 25, 2013.

* cited by examiner

ELECTRONIC ENDOSCOPE SYSTEM WITH OXYGEN SATURATION ENHANCING IMAGE REGION

BACKGROUND OF INVENTION

The present invention relates to an electronic endoscope system for acquiring information on a blood vessel from an image acquired by an electronic endoscope and producing an image from the acquired information.

In recent years, a number of diagnoses and treatments using electronic endoscopes have been made in the field of medicine. A typical electronic endoscope is equipped with an elongated insertion section that is inserted into a subject's body cavity. The insertion section has therein incorporated an imager such as a CCD at the tip thereof. The electronic endoscope is connected to a light source device, which emits light from the tip of the insertion section to illuminate the inside of a body cavity. With the inside of the body cavity illuminated by light, the subject tissue inside the body cavity is imaged by an imager provided at the tip of the insertion section. Images acquired by imaging undergoes various kinds of processing by a processor connected to the electronic endoscope before being displayed by a monitor. Thus, the electronic endoscope permits real-time observation of images showing the inside of the subject's body cavity and thus enables sure diagnoses.

The light source device uses a white light source such as a xenon lamp capable of emitting white broadband light whose wavelength ranges from a blue region to a red region. Use of white broadband light to illuminate the inside of a body cavity permits observing the whole subject tissue from the acquired images thereof.

However, although images acquired by broadband light illumination permit generally observing the whole subject tissue, there are cases where such images fail to enable clear observation of subject tissues such as micro-blood vessels, deep-layer blood vessels, pit patterns, and uneven surface profiles formed of recesses and bumps.

As is known, such subject tissues may be made clearly observable when illuminated by narrowband light having a wavelength limited to a specific range. As is also known, image data obtained by illumination with narrowband light yields various kinds of information on a subject tissue such as oxygen saturation level in a blood vessel.

For example, JP 2660009 B comprises filters each exclusively corresponding to their respective wavelength ranges for a color image (normal image), an oxygen saturation level image, and a blood vessel distribution image produced using ICG fluorescence, respectively, permitting selective display of such images and, hence, comparison between, for example, a special image containing blood information and a normal visible-wavelength image.

SUMMARY OF INVENTION

In recent years, there are demands for a system permitting not only a diagnosis accompanied by simultaneous observation of both a normal visible-wavelength image and a special image containing blood information such as oxygen saturation level but also a diagnosis that allows an observer to selectively display an oxygen saturation level of a characteristic blood vessel portion that is of particular interest to the observer in making a diagnosis. However, there have never been provided diagnoses where the observers selectively displayed a portion that is of diagnostic interest.

For example, JP 2648494 B, comprising filters exclusively corresponding to their respective wavelength ranges, permits separate acquisition of a color image, an oxygen saturation level image, and a blood vessel distribution image produced using ICG fluorescence, by switching between the filters but does not have a configuration that permits selective display of an oxygen saturation level of a characteristic blood vessel portion that is of interest to the observer in making a diagnosis.

An object of the present invention is to provide an electronic endoscope system that enables simultaneous acquisition of both blood vessel depth information and oxygen saturation level information and selective display of an oxygen saturation level of a characteristic blood vessel portion that is of interest to an observer in making a diagnosis.

To achieve the above objects, the present invention provides an electronic endoscope system comprising a light source device for sequentially emitting plural kinds of light having different wavelength bands from each other; an electronic endoscope for sequentially illuminating the plural kinds of light emitted from said light source device to a subject tissue containing blood vessels inside a body cavity, sequentially receiving the plural kinds of reflected light of the illuminated light from the subject tissue, and sequentially outputting image data of acquired images corresponding to the plural kinds of received light having the different wavelength bands; blood vessel characteristics amount setting means for setting a blood vessel characteristics amount related to the blood vessel containing at least one of a diameter of the blood vessel, a density of the blood vessel, and a branch point density of the blood vessel from the image data of at least one of the acquired image outputted from said electronic endoscope; interest region setting means for setting a region of interest in the acquired image by said electronic endoscope based on the blood vessel characteristics amount calculated by said blood vessel characteristics amount setting means; image production means for producing a first oxygen saturation level image representing a distribution of an oxygen saturation level in the blood vessel in simulated color from the image data of the acquired images; and image display means for displaying in the simulated color a second oxygen saturation level image in which the oxygen saturation level within the region of interest set by said interest region setting means is selectively enhanced in the first oxygen saturation level image produced by said image production means.

Preferably, the blood vessel characteristics amount setting means sets the diameter of the blood vessel as the blood vessel characteristics amount and the interest region setting means sets a region of the blood vessel having a given diameter as the region of interest.

Preferably, the interest region setting means sets a region of micro blood vessel having a diameter of 10 nm to 20 nm as the region of interest.

Preferably, the blood vessel characteristics amount setting means sets the density of the blood vessel as the blood vessel characteristics amount and the interest region setting means sets a region of the blood vessel having a density greater than a given threshold value as the region of interest.

Preferably, the blood vessel characteristics amount setting means sets the branch point density of the blood vessel as the blood vessel characteristics amount and the interest region setting means sets a region of the blood vessel having a branch point density of the blood vessel greater than a given threshold value as the region of interest.

Preferably, the electronic endoscope system further comprises second image production means for producing the second oxygen saturation level image in which the oxygen saturation level within the region of interest is enhanced, and the image display means displays in the simulated color the second oxygen saturation level image produced by said second image production means.

Preferably, the second image production means increases a color saturation of the oxygen saturation level in the simulated color within the region of interest to selectively enhance the oxygen saturation level within the region of interest in the second oxygen saturation level image.

The present invention, provided with both a blood vessel characteristics amount setting means and an oxygen saturation level setting means, permits selective display of an oxygen saturation level of a characteristic blood vessel portion that is of diagnostic interest.

DETAILED DESCRIPTION OF INVENTION

Figure 1:
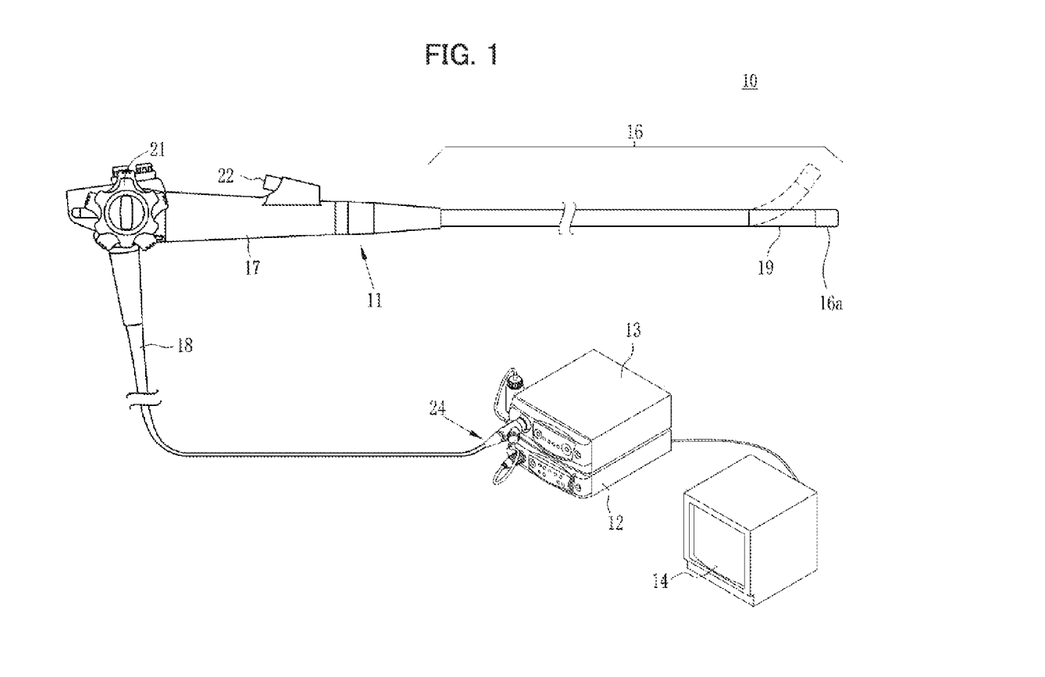
FIG. 1 is an external view of an electronic endoscope system according to a first embodiment of the invention.

As illustrated in FIG. 1, an electronic endoscope system 10 according to the first embodiment of the invention comprises an electronic endoscope 11 for imaging the inside of a subject's body cavity, a processor 12 for producing an image of a subject tissue in the body cavity based on a signal acquired by imaging, a light source device 13 for supplying light used to illuminate the inside of the body cavity, and a monitor (image display means) 14 for displaying the image of the inside of the body cavity. The electronic endoscope 11 comprises a flexible insertion section 16 that is inserted into a body cavity, an operating section 17 provided at the base of the insertion section 16, and a universal cord 18 for connecting the operating section 17 to the processor 12 and the light source device 13.

The insertion section 16 has a bending portion 19 at the tip thereof comprising connected bending pieces. The bending portion 19 bends up and down, left and right in response to the operation of an angle knob 21 of the operating section 17. The bending portion 19 has at its tip a leading end portion 16a incorporating an optical system and other components for imaging the inside of a body cavity. The leading end portion 16a can be directed in a desired direction in the body cavity according to a bending operation of the bending portion 19.

The universal cord 18 has a connector 24 provided on the side thereof leading to the processor 12 and the light source device 13. The connector 24 is a composite type connector composed of a communication connector and a light source connector and removably connects the electronic endoscope 11 to the processor 12 and the light source device 13 through the connector 24.

Figure 2:
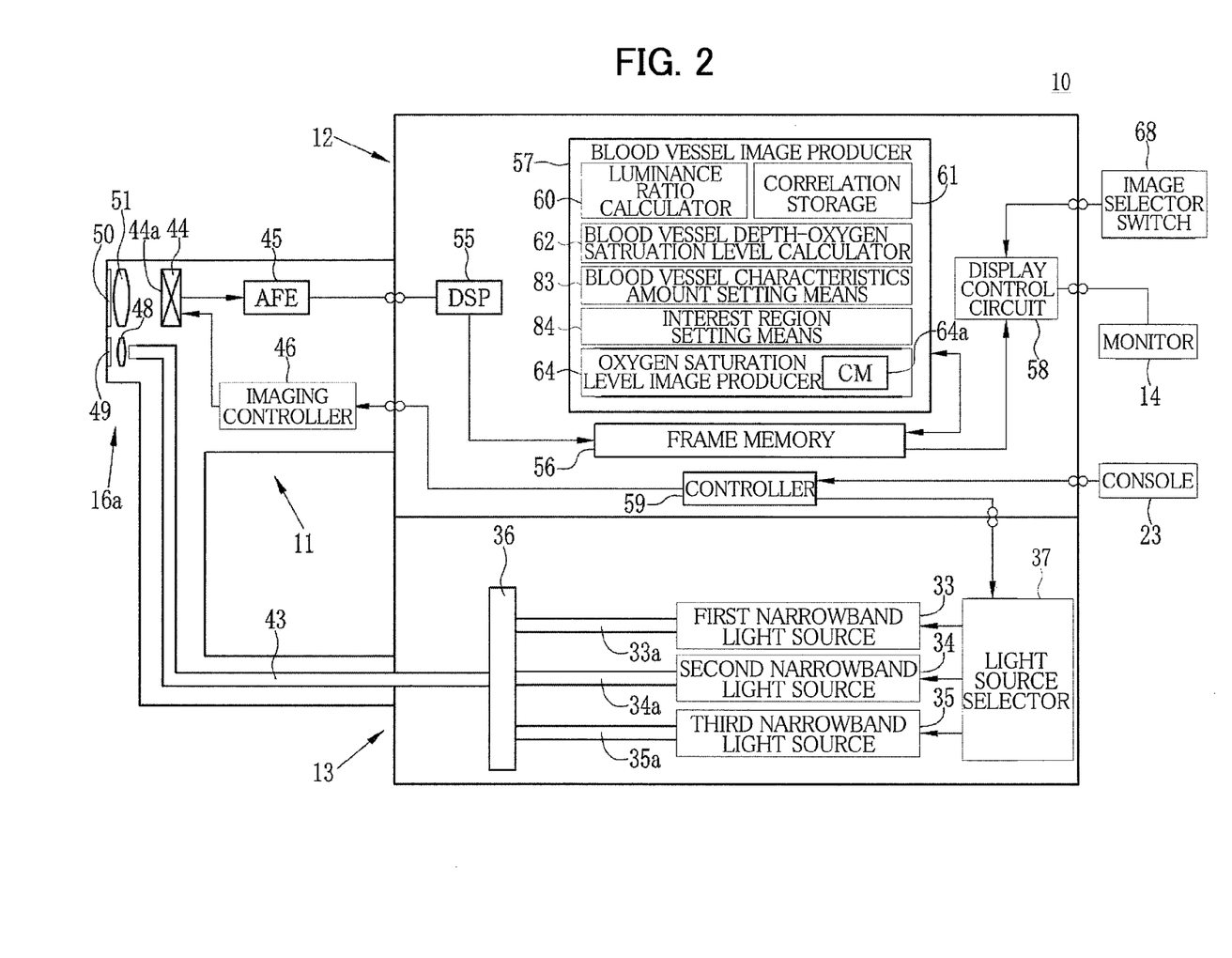
FIG. 2 is a block diagram illustrating an electric configuration of the electronic endoscope system according to a second embodiment of the invention.

As illustrated in FIG. 2, the light source device 13 comprises first to third narrowband light sources 33 to 35, a coupler 36, and a light source selector 37.

The first to the third narrowband light sources 33 to 35 are laser diodes or the like. The first narrowband light source 33 produces narrowband light having a wavelength limited to 440 nm+/−10 nm, preferably 445 nm (referred to below as "first narrowband light N1"), the second narrowband light source 34 produces narrowband light having a wavelength limited to 470 nm+/−10 nm, preferably 473 nm (referred to below as "second narrowband light N2"), and the third narrowband light source 35 produces narrowband light having a wavelength limited to 400 nm+/−10 nm, preferably 405 nm (referred to below as "third narrowband light N3"). The first to the third narrowband light sources 33 to 35 are connected respectively to first to third narrowband optical fibers 33a to 35a, allowing the first to the third narrowband light N1 to N3 emitted by their respective light sources to enter the first to the third narrowband optical fibers 33a to 35a.

The coupler 36 connects a light guide 43 in the electronic endoscope to the first to the third narrowband optical fibers 33a to 35a. The first to the third narrowband light N1 to N3 can enter the light guide 43 through the first to the third narrowband optical fibers 33a to 35a.

The light source selector 37 is connected to the controller 59 in the processor and turns on or off the first to the third narrowband light sources 33 to 35 according to an instruction by the controller 59. According to the first embodiment, the first to the third narrowband light sources 33 to 35 are sequentially turned on to permit imaging using the first to the third narrowband light N1 to N3.

Specifically, the light source selector 37 first turns on the first narrowband light source 33. Then, imaging of the subject tissue is started with the first narrowband light N1 illuminating the inside of the body cavity. Upon completion of imaging, the controller 59 gives a light source switching instruction to turn off the first narrowband light source 33 and turn on the second narrowband light source 34. Likewise, upon completion of imaging with the second narrowband light N2 illuminating the inside of the body cavity, the second narrowband light source 34 is turned off and the third narrowband light source 35 is turned on. Upon completion of imaging with the third narrowband light N3 illuminating the inside of the body cavity, the third narrowband light source 35 is turned off.

The electronic endoscope 11 comprises a light guide 43, a CCD 44, an analog processing circuit (AFE: analog front end) 45, and an imaging controller 46. The light guide 43 is a large-diameter optical fiber, a bundle fiber, or the like having its light-receiving end inserted in the coupler 36 in the light source device, whereas its light emitting end is directed toward an illumination lens 48 located in the leading end portion 16a. The light emitted by the light source device 13 is guided by the light guide 43 and emitted toward the illumination lens 48. The light admitted in the illumination lens 48 passes through an illumination window 49 attached to the end face of the leading end portion 16a to enter the body cavity. The first to the third narrowband light N1 to N3 reflected by the inside of the body cavity pass through an observation window 50 attached to the end face of the leading end portion 16a to enter a condenser lens 51.

The CCD 44 receives the light from the condenser lens 51 with its imaging surface 44a, performs photoelectric conversion of the received light to accumulate a signal charge, and reads out the accumulated signal charge as an imaging signal. The read-out imaging signal is transmitted to an AFE 45.

The first narrowband light N1 to the third narrowband light N3 enter the CCD 44 to produce a first narrowband imaging signal to a third narrowband imaging signal.

The AFE 45 comprises a correlated double sampling circuit (CDS), an automatic gain control circuit (AGC), and an analog-to-digital converter (A/D) (none of them are shown). The CDS performs correlated double sampling of an imaging signal supplied from the CCD 44 to remove noise generated by actuation of the CCD 44. The AGC amplifies an imaging signal from which noise has been removed by the CDS. The analog-to-digital converter converts an imaging signal amplified by the AGC into a digital imaging signal having a given number of bits, which is applied to the processor 12.

The imaging controller 46 is connected to the controller 59 in the processor 12 and sends a drive signal to the CCD 44 in response to an instruction given by the controller 59. The CCD 44 outputs an imaging signal to the AFE 45 at a given frame rate according to the drive signal from the imaging controller 46.

Figure 3:
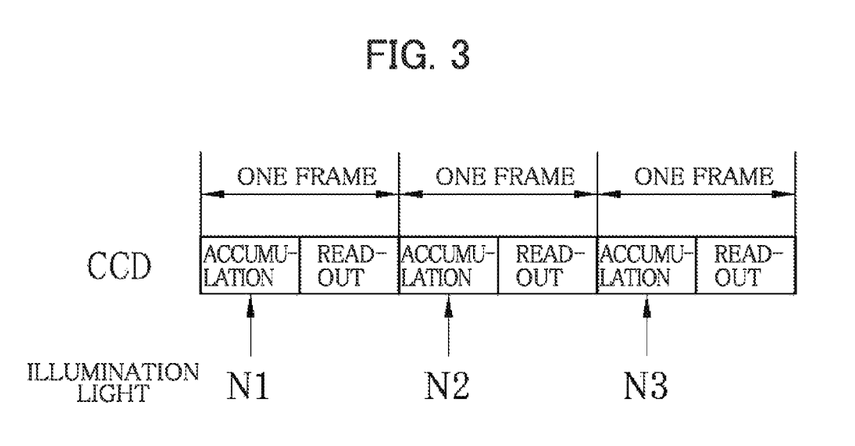
FIG. 3 is a view for explaining imaging operations of a CCD according to the invention.

As illustrated in FIG. 3, a total of two operations are first performed in one frame of acquisition period: a step of accumulating a signal charge through photoelectric conversion of the first narrowband light N1 and a step of reading out the accumulated signal charge as a first narrowband imaging signal. Upon completion of readout of the first narrowband imaging signal, a step of accumulating a signal charge through photoelectric conversion of the second narrowband light N2 and a step of reading out the accumulated signal charge as a second narrowband imaging signal are performed in one frame of acquisition period. Upon completion of readout of the second narrowband imaging signal, a step of accumulating a signal charge through photoelectric conversion of the third narrowband light N3 and a step of reading out the accumulated signal charge as a third narrowband imaging signal are performed in one frame of acquisition period.

As illustrated in FIG. 2, the processor 12 comprises a digital signal processor 55 (DSP), a frame memory 56, a blood vessel image producer 57 (image producing means), and a display control circuit 58, all of these components being controlled by the controller 59. The DSP 55 performs color separation, color interpolation, white balance adjustment, gamma correction, and the like of the first to the third narrowband imaging signals produced from the AFE 45 of the electronic endoscope to produce the first to the third narrowband image data. The frame memory 56 stores the first to the third narrowband image data produced by the DSP 55.

The blood vessel image producer 57 comprises a luminance ratio calculator 60, a correlation storage 61, a blood vessel depth-oxygen saturation level calculator 62, an oxygen saturation level image producer 64, a blood vessel characteristics amount setting means 83, and a region-of-interest setting means 84. The luminance ratio calculator 60 determines a blood vessel region containing a blood vessel from the first to the third narrowband image data stored in the frame memory 56. The luminance ratio calculator 60 obtains a first luminance ratio S1/S3 between the first and the third narrowband image data and a second luminance ratio S2/S3 between the second and the third narrowband image data corresponding to a pixel at the same position in the blood vessel region. S1 is a luminance of a pixel of the first narrowband image data, S2 a luminance of a pixel of the second narrowband image data, and S3 a luminance of a pixel of the third narrowband image data. The blood vessel region may be determined, for example, by a method whereby the blood vessel region is obtained from the difference between the luminance of a blood vessel of interest and the luminance of the other region.

Figure 4:
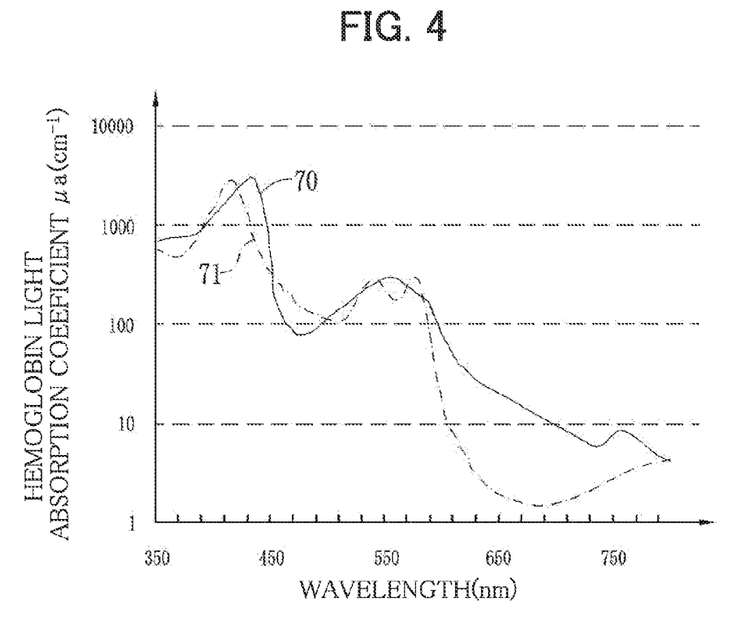
FIG. 4 is a graph illustrating an absorption coefficient of hemoglobin.

The correlation storage 61 stores a correlation between the first and the second luminance ratios S1/S3 and S2/S3 on the one hand and an oxygen saturation level in a blood vessel and a blood vessel depth on the other hand. That correlation is one where a blood vessel contains hemoglobin exhibiting light absorption coefficients as shown in FIG. 4 and is obtained by analyzing, for example, a number of the first to the third narrowband image data accumulated through diagnoses hitherto made. As illustrated in FIG. 4, the hemoglobins in a blood vessel have light absorptions characteristics having the light absorption coefficient $\mu a$ changing according to the wavelength of light used for illumination. The light absorption coefficient $\mu a$ indicates an absorbance, i.e., a degree of light absorption by hemoglobin, and is a coefficient in an expression $I0\exp(-\mu a \times x)$ showing the attenuation of light illuminating the hemoglobin. In this expression, Io is the intensity of light emitted from the light source device to illuminate a subject tissue; x (cm) is a depth of a blood vessel inside the subject tissue.

A reduced hemoglobin 70 and an oxygenated hemoglobin 71 have different light absorption characteristics such that they have different absorbances except for the isosbestic point at which both exhibit the same absorbance (intersection of light absorption characteristics curves of hemoglobins 70 and 71 in FIG. 4). With a difference in absorbance, the luminance varies even when the same blood vessel is illuminated by light having the same intensity and the same wavelength. The luminance also varies when the illumination light has the same intensity but varies in wavelength because a difference in wavelength causes the light absorption coefficient $\mu a$ to change.

In view of the light absorption characteristics of hemoglobin as described above and considering the fact that wavelengths whereby the absorbance varies according to the oxygen saturation level lie in a range of 445 nm and 504 nm and that light having a short wavelength and hence having a short reaching depth is required in order to retrieve blood vessel depth information, at least one of the first to the third narrowband light N1 to N3 preferably has a wavelength range whose central wavelength is 450 nm or less. According to the first embodiment of the invention, the first and the second narrowband light are such narrowband light. Further, with the same oxygen saturation level, a difference in wavelength causes a difference in absorption coefficient and also a difference in reaching depth into a mucus membrane. Therefore, using the property of light whose reaching depth varies with the wavelength permits obtaining correlation between luminance ratio and blood vessel depth.

Figure 5:
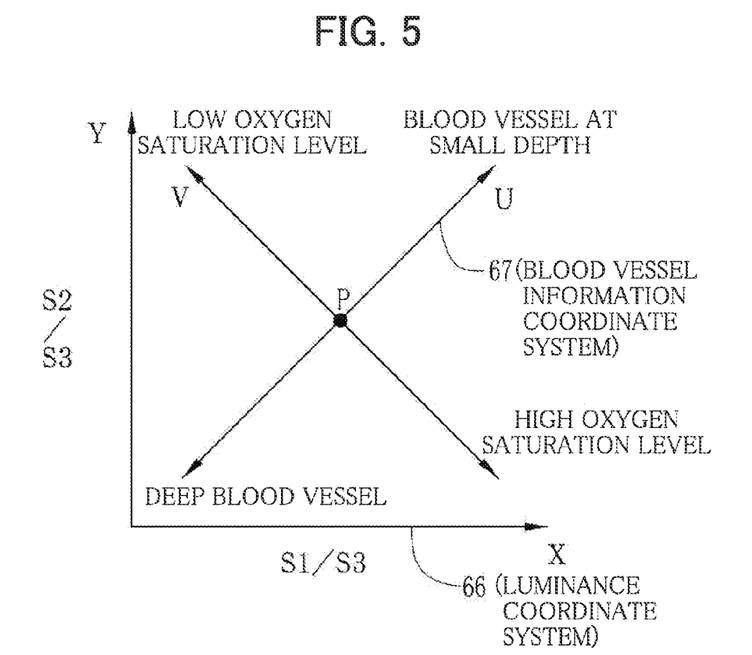
FIG. 5 is a graph illustrating a correlation between first and second luminance ratios S1/S3 and S2/S3 on the one hand and blood vessel depth and oxygen saturation level on the other hand.

As illustrated in FIG. 5, the correlation storage 61 stores a correlation in correspondence between the coordinate points in a luminance coordinate system 66 representing the first and the second luminance ratios S1/S3 and S2/S3 and the coordinate points in a blood vessel information coordinate system 67 representing oxygen saturation level and blood vessel depth. The luminance coordinate system 66 is an XY coordinate system, where the X axis shows the first luminance ratio S1/S3 and the Y axis shows the second luminance ratio S2/S3. The blood vessel information coordinate system 67 is a UV coordinate system provided on the luminance coordinate system 66, where the U axis shows the blood vessel depth and the V axis shows the oxygen saturation level. Because the blood vessel depth has a positive correlation with the luminance coordinate system 66, the U axis has a positive slope. The U axis shows that a blood vessel of interest is located at an increasingly smaller depth as a position on the U axis moves obliquely up rightward and that a blood vessel of interest is located at an increasingly greater depth as a position on the U axis moves obliquely down leftward. On the other hand, because the oxygen saturation level has a negative correlation with the luminance coordinate system 66, the V axis has a negative slope. The V axis shows that the oxygen saturation level is lower as a position on the V axis moves obliquely up leftward and that the oxygen saturation level is higher as a position on the V axis moves obliquely down rightward.

In the blood vessel information coordinate system 67, the U axis and the V axis cross each other at right angles at an intersection P. This is because the magnitude of absorbance reverses between illumination by the first narrowband light N1 and illumination by the second narrowband light N2. More specifically, as illustrated in FIG. 4, illumination by the first narrowband light N1 having a wavelength of 440 nm+/−10 nm allows the light absorption coefficient of the reduced hemoglobin 70 to be greater than that of the oxygenated hemoglobin 71 having a high oxygen saturation level whereas illumination by the second narrowband light N2 having a wavelength of 470 nm+/−10 nm allows the light absorption coefficient of the oxygenated hemoglobin 71 to be greater than that of the reduced hemoglobin 70 having a high oxygen saturation level, thus causing the magnitude of the absorbance to reverse.

When narrowband light permitting no absorbance reversal are used in lieu of the first to the third narrowband light N1 to N3, the U axis and the V axis do not cross each other at right angles. With illumination provided by the third narrowband light N3 having a wavelength of 400 nm+/−10 nm, the oxygenated hemoglobin and the reduced hemoglobin have a substantially equal light absorption coefficient.

The blood vessel depth-oxygen saturation level calculator 62 determines an oxygen saturation level and a blood vessel depth corresponding to the first and the second luminance ratios S1/S3 and S2/S3 calculated by the luminance ratio calculator 60 based on the correlation stored in the correlation storage 61. Now, in the first and the second luminance ratios S1/S3 and S2/S3 calculated by the luminance ratio calculator 60, let S1*/S3* and S2*/S3* be the first luminance ratio and the second luminance ratio respectively for a given pixel in the blood vessel region.

Figure 6A:
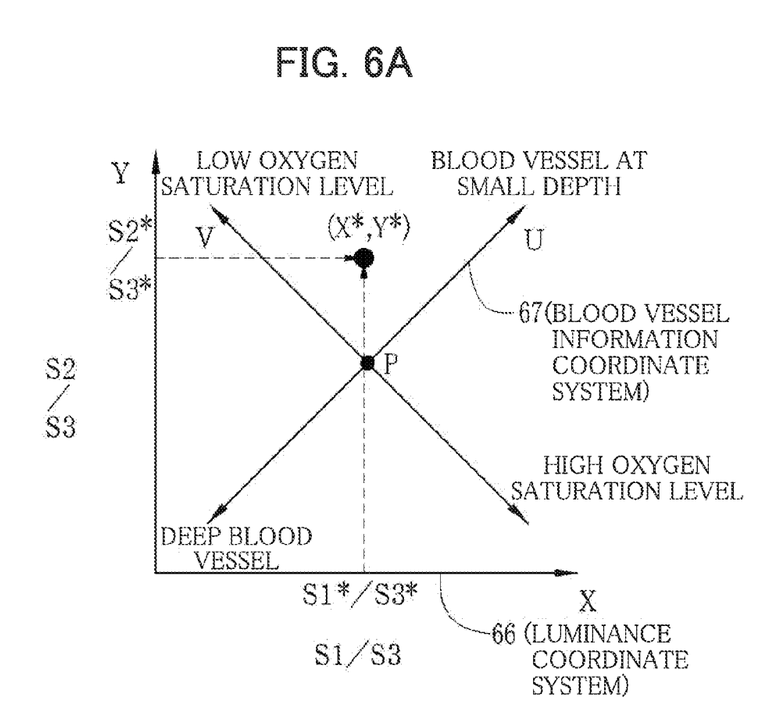
FIG. 6A is a view for explaining how a coordinate point (X*, Y*) in a luminance coordinate system is obtained from the first and the second luminance ratios S1*/S3* and S2*/S3*.
Figure 6B:
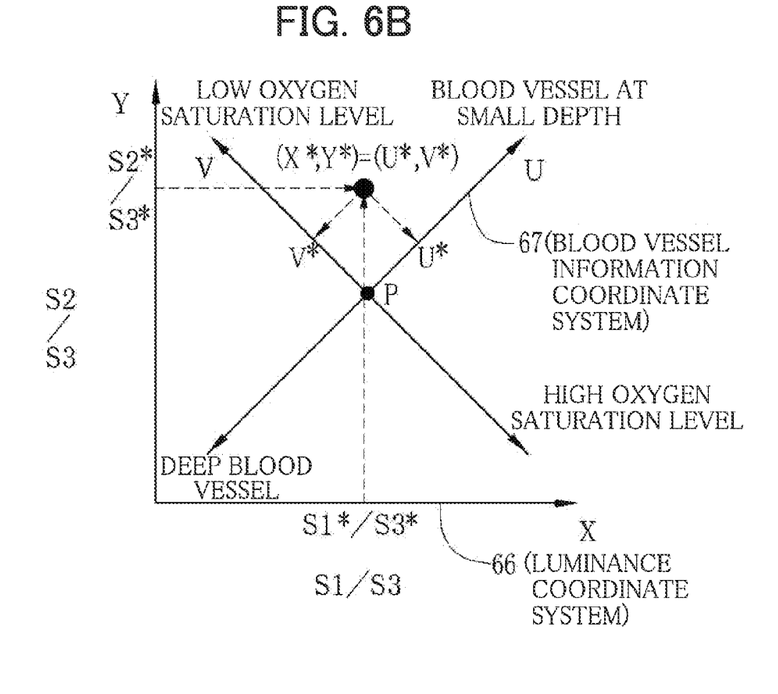
FIG. 6B is a view for explaining how a coordinate point (U*, V*) in a blood vessel information coordinate system corresponding to the coordinate point (X*, Y*) is obtained.

As illustrated in FIG. 6A, the blood vessel depth-oxygen saturation level calculator 62 determines a coordinate point (X*,Y*) corresponding to the first and the second luminance ratios S1*/S3* and S2*/S3* in the luminance coordinate system 66. Upon the coordinate point (X*, Y*) being determined, the blood vessel information coordinate system 62 determines a coordinate point (U*, V*) corresponding to the coordinate point (X*, Y*) in the blood vessel information coordinate system 67 as illustrated in FIG. 6B. Thus, blood vessel depth information U* and oxygen saturation level information V* are obtained for a given pixel in the blood region.

The oxygen saturation level image producer 64 has a color map 64a (CM) where oxygen saturation levels are assigned color information. More specifically, the color map 64a permits easy distinction of oxygen saturation level by color assignment (assignment of simulated color (assignment of false color or pseudo color)) such that, for example, a low oxygen saturation level is assigned a color of cyan, a medium oxygen saturation level is assigned a color of magenta, and a high oxygen saturation level is assigned a color of yellow. From the color map 64a, the oxygen saturation level image producer 64 determines color information corresponding to the oxygen saturation level information V* calculated by the blood vessel depth-oxygen saturation level calculator. Then, this color information is determined for all the images in the blood vessel region and incorporated by, for example, superimposition, for the first narrowband image data, that is to say, by combining the first narrowband image with an image of color information, to produce image data of the oxygen saturation level image representing the oxygen saturation level in simulated color.

The oxygen saturation level image data thus produced is stored in the frame memory 56.

According to the invention, the oxygen saturation level image producer 64 enhances, for the thus produced oxygen saturation level image data, the color information corresponding to the oxygen saturation level information V*, i.e., the color saturation of a color representing a color saturation level, e.g., cyan, which represents a low oxygen level, in a region of interest that is set by the interest region setting means 84, e.g., a region containing micro-blood vessels of about 10 μm to 20 μm, for the oxygen saturation level image data produced, to produce image data of enhanced oxygen saturation level image where the oxygen saturation level in the micro-blood vessel is selectively enhanced. The enhanced oxygen saturation level image data thus produced is stored in the frame memory 56.

The method of enhancing the color saturation of the color information in a region of interest is not specifically limited but it is preferable that the color information of the color map 64a is set in such a manner that the color saturation of color information corresponding to the oxygen saturation level information is enhanced in a region of interest to be set and that the color saturation of the color information in a region of interest that was set is enhanced for the oxygen saturation level image data using the color map 64a.

When a region of interest set by the interest region setting means 84 is produced as region of interest setting image data represented as, for example, a binarized image, the oxygen saturation level image producer 64 may make such settings as to enhance the color saturation of the color information in the region of interest for the oxygen saturation level image data and the region-of-interest setting image data using the color map 64a to produce image data of an enhanced oxygen saturation level image where the oxygen saturation level in a region of interest is selectively enhanced. Further, in lieu of using the oxygen saturation level image data, the oxygen saturation level image producer 64 may use the first narrowband image data to incorporate color information corresponding to the oxygen saturation level information V* and color information having a color saturation corresponding to the oxygen saturation level information V* and set region information enhanced in the color map 64a in the first narrowband image data thereby to produce image data of an enhanced oxygen saturation level image where the oxygen saturation level in a region of interest is selectively enhanced.

Further, the image selector switch 68 may be provided with a color display change means to enable the observer to set the enhancement of the color information corresponding to the oxygen saturation level information and/or the color information corresponding to the set region information while observing the enhanced oxygen saturation level image displayed on the monitor 14. The method of selectively enhancing the oxygen saturation level in a set region is not limited to the method of enhancing the color saturation of the color information corresponding to the oxygen saturation level information, provided that display can be made with enhancement and thus is not specifically limited, permitting a method whereby enhancement is selectively achieved by changing the hue or luminosity.

The blood vessel characteristics amount setting means 83 sets a characteristic amount (blood vessel characteristics amount) related to a blood vessel to be enhanced in the first to the third narrowband image data. According to this embodiment, the blood vessel characteristics amount in the first narrowband image data that is set is the diameter of a blood vessel.

As described later, the blood vessel characteristics amount may be a blood vessel density, a blood vessel branch point density, or the like in lieu of the diameter of a blood vessel.

The region-of-interest setting means 84 sets a region of interest in the first narrowband image based on the blood vessel characteristics amount that is set by the blood vessel characteristics amount setting means 83.

The region of interest according to this embodiment is a region of a blood vessel enhanced in respect of the blood vessel characteristics amount in an image acquired by the electronic endoscope 11. According to this embodiment, a region or a neighborhood of a region containing micro-blood vessels of which the diameter that is set as the blood vessel characteristics amount is about 10 μm to 20 μm representing a characteristic blood vessel portion of diagnostic interest is set as a region of interest.

First, the first narrowband image data stored in the frame memory 56 is acquired, and then a micro blood vessel having a diameter of about 10 μm to 20 μm is extracted in the first narrowband image data. The extraction of a blood vessel having a diameter of about 10 μm to 20 μm is achieved by acquiring and enhancing a signal of a frequency component corresponding to this diameter.

A signal of a particular frequency component may be extracted using for example a two-dimensional filter.

To produce such a two-dimensional filter, first the frequency band in an image corresponding to the diameter of the micro blood vessel (measuring 10 μm to 20 μm in diameter) is obtained by estimating a distance and a magnification ratio between the leading end portion 16a of the endoscope and the subject. Next, a filter that enhances only that frequency band is designed in frequency space and then adapted to correspond to real space through Fourier transformation. In the present case, the filter characteristics need to be adjusted in frequency space so that the size of the filter can be contained within a realistic size of say about 5×5.

Application of the two-dimensional filter thus produced to the first narrowband image data permits extraction of a micro blood vessel having a diameter of about 10 μm to 20 μm. Thus, the region-of-interest setting means 84 sets extracted micro-blood vessels as a region of interest.

Then, the region-of-interest setting means 84 produces data representing a region or a position containing extracted micro-blood vessels as a region of interest setting data and stores the data in the frame memory 56. The region of interest setting data is stored in association with the first narrowband image data. For example, the region of interest setting data may be region of interest setting data representing, as an image, a region of interest that is set in the first narrowband image having micro-blood vessels extracted.

Figure 7:
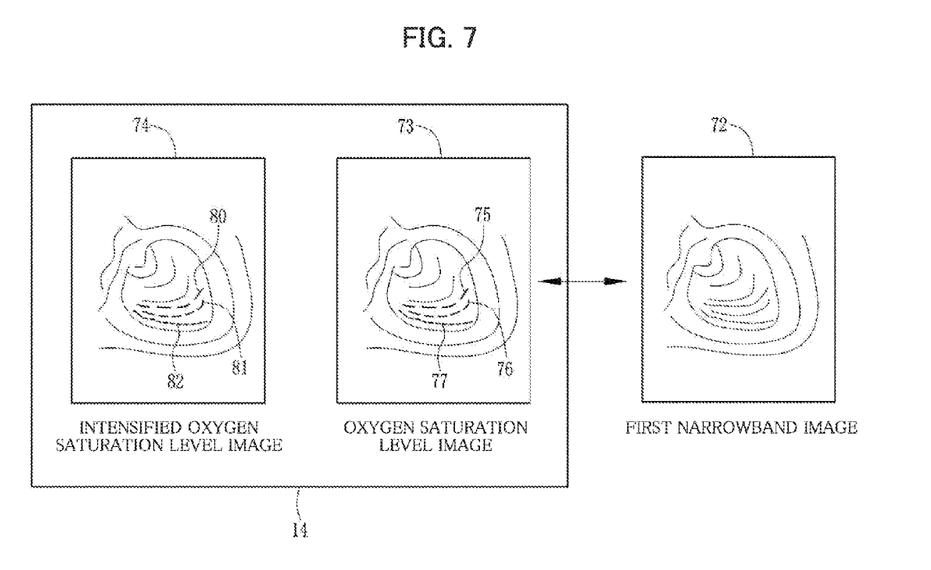
FIG. 7 illustrates an image view of a screen given by a monitor displaying an enhanced oxygen saturation level image and either of a first narrowband image and an oxygen saturation level image.

The display control circuit 58 reads out image data of one or more images from the frame memory 56 and allows the monitor 14 to display the read-out image or images. The images may be displayed in various modes. As illustrated in FIG. 7, for example, the monitor 14 may display an enhanced oxygen saturation level image 72 on one side and either of the first narrowband image 72 and the oxygen saturation level image 73 selected by the image selector switch 68 (see FIG. 2) on the other side. In the oxygen saturation level image 73 illustrated in FIGS. 7 and 8, a blood vessel image 75, for example, is displayed in cyan indicating a lower oxygen saturation level, a blood vessel image 76 is displayed in magenta indicating a medium oxygen saturation level; and a blood vessel image 77 is displayed in yellow indicating a higher oxygen saturation level. In the enhanced oxygen saturation level image 74 illustrated in FIGS. 7 and 8, the color saturation of the oxygen saturation level in a region of interest such as a micro-blood vessel region is set to a high value: for example, a blood vessel image 80 is displayed in enhanced cyan indicating a low oxygen saturation level in a region of interest; a blood vessel image 81 is displayed in enhanced cyan indicating a medium oxygen saturation level in a region of interest; and a blood vessel image 82 is displayed in enhanced yellow indicating a high oxygen saturation level in a region of interest.

Figure 8:
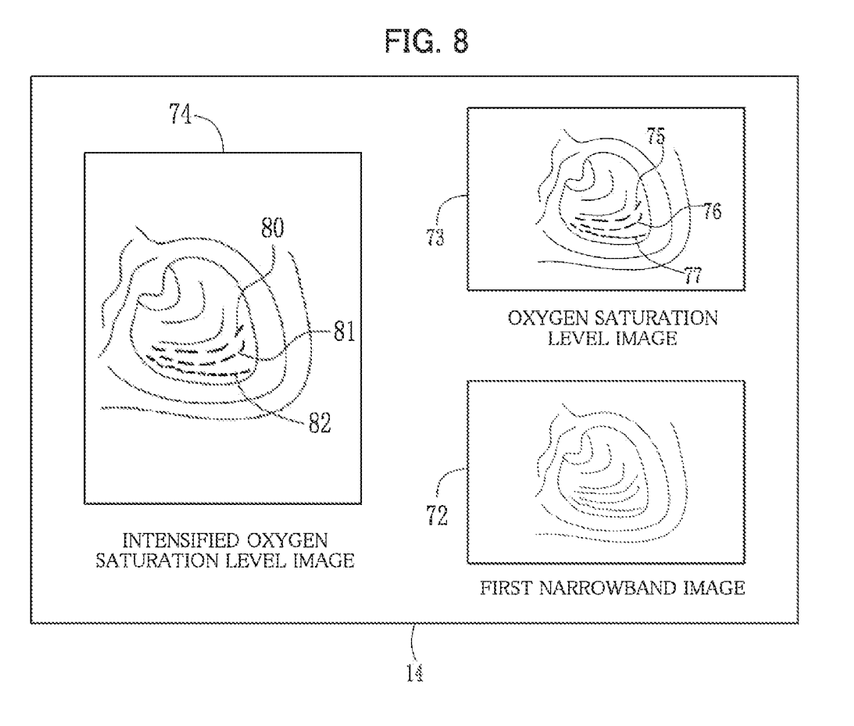
FIG. 8 illustrates an image view of a screen given by a monitor displaying an enhanced oxygen saturation level image, the first narrowband image, and an oxygen saturation level image.

In contrast with the display mode shown in FIG. 7, the enhanced oxygen saturation level image 74 and the oxygen saturation level image 73 may be both displayed simultaneously as illustrated in FIG. 8.

Figure 9:
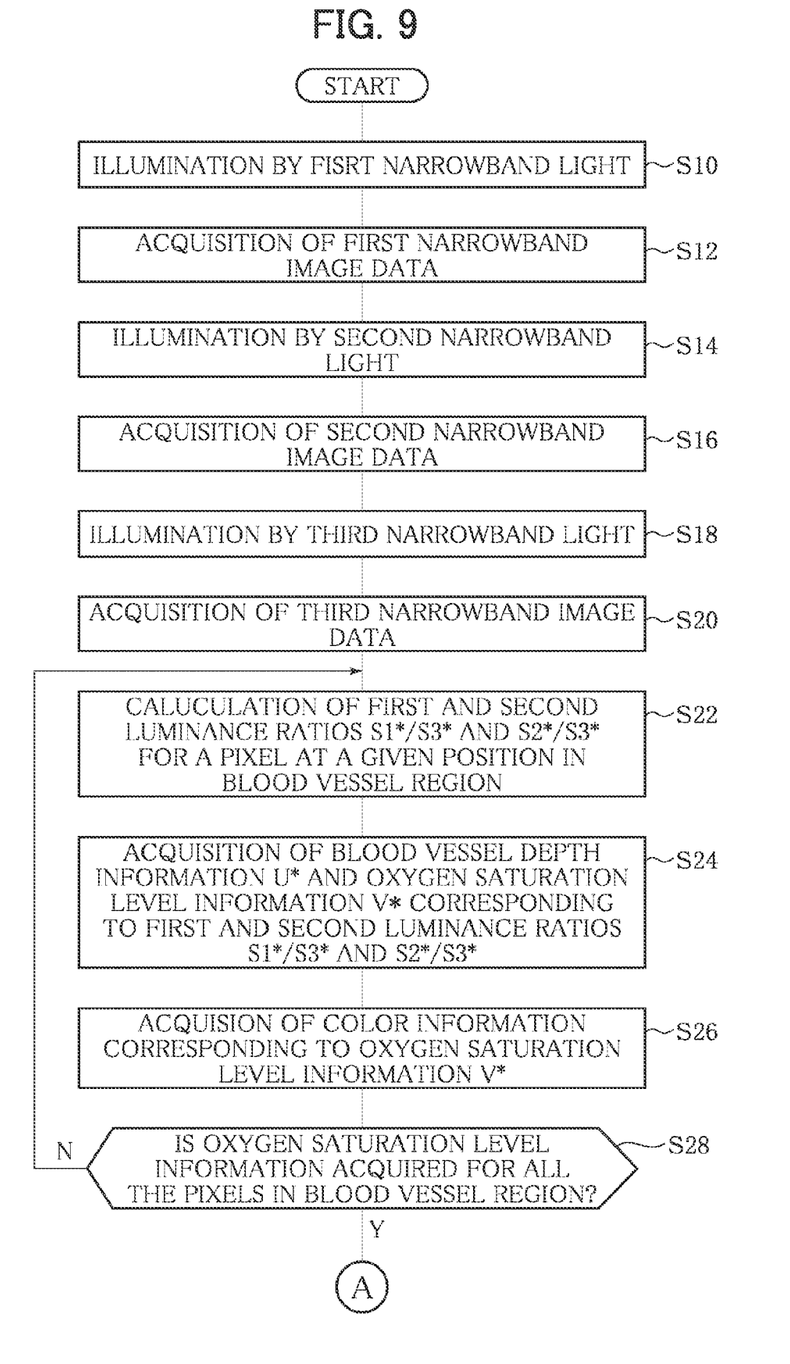
FIG. 9 is the first half of the flow chart illustrating a procedure of calculating blood vessel depth-oxygen saturation level information, a procedure of specifying a region of interest, and a procedure of producing an oxygen saturation level image and an enhanced oxygen saturation level image incorporating that information.

Next, we will describe a procedure of calculating the blood vessel depth-oxygen saturation level information and a procedure of producing the oxygen saturation level image and the enhanced oxygen saturation level image incorporating such oxygen saturation level information referring to the flowchart illustrated in FIG. 9.

First, the console 23 is operated so that the light source selector 37 turns on the first narrowband light source 33 to illuminate the inside of the body cavity with the first narrowband light N1. Upon the narrowband light N1 illuminating the inside of the body cavity, the controller 59 sends the imaging controller 46 an imaging instruction. Thus, imaging is done by illumination with the first narrowband light N1, and the first narrowband imaging signal obtained by the imaging is sent through the AFE 45 to the DSP 55. The DSP 55 produces the first narrowband image data based on the first narrowband imaging signal. The first narrowband image data thus produced is stored in the frame memory 56. As described below, the oxygen saturation image and the enhanced oxygen saturation image are produced based on the first narrowband image data.

When the first narrowband image data has been stored in the frame memory 56, the light source selector 37 switches the light for illuminating the inside of the body cavity from the first narrowband light N1 to the second narrowband light N2 in response to the light source switching instruction from the controller 59. Then, imaging is done similarly to the case using the first narrowband light N1 to produce the second narrowband image data based on the second narrowband imaging signal obtained by the imaging. The second narrowband image data thus produced is stored in the frame memory 56.

When the second narrowband image data has been stored in the frame memory 56, the light source selector 37 switches the light for illuminating the inside of the body cavity from the second narrowband light N2 to the third narrowband light N3 in response to the light source switching instruction from the controller 59. Then, imaging is done similarly to the cases using the first and the second narrowband light N1 and N2 to produce the third narrowband image data based on the third narrowband imaging signal obtained by the imaging. The third narrowband image data thus produced is stored in the frame memory 56.

When the first to the third narrowband image data have been stored in the frame memory 56, the luminance ratio calculator 60 determines the blood vessel region containing a blood vessel from three image data, i.e., the first narrowband image data, the second narrowband image data, and the third narrowband image data. Then, the luminance ratio calculator 60 calculates the first luminance ratio S1*/S3* between the first and the third narrowband image data and the second luminance ratio S2*/S3* between the second and the third narrowband image data corresponding to a pixel at the same position in the blood vessel region.

Next, the blood vessel depth-oxygen saturation level calculator 62 determines the coordinate point (X*, y*) in the luminance coordinate system corresponding to the first and the second luminance ratios S1*/S3* and S2*/S3* based on the correlation stored in the correlation storage 61. Further, the coordinate point (U*, V*) in the blood vessel information coordinate system corresponding to the coordinate point (X*, y*) is determined to obtain the blood vessel depth information U* and the oxygen saturation level information V* for a given pixel in the blood vessel region.

When the blood vessel depth information U* and the oxygen saturation level information V* have been obtained, color information corresponding to the oxygen saturation level information V* is determined from the color map 64a in the oxygen saturation level image producer 64. The color information thus determined are stored in the RAM (not shown) in the processor 12.

Upon storage of the color information in the RAM, the above procedure is followed to obtain the oxygen saturation level information V* for all the pixels in the blood vessel region, determine color information corresponding to the oxygen saturation level information V*, which is then stored in the RAM.

Figure 10:
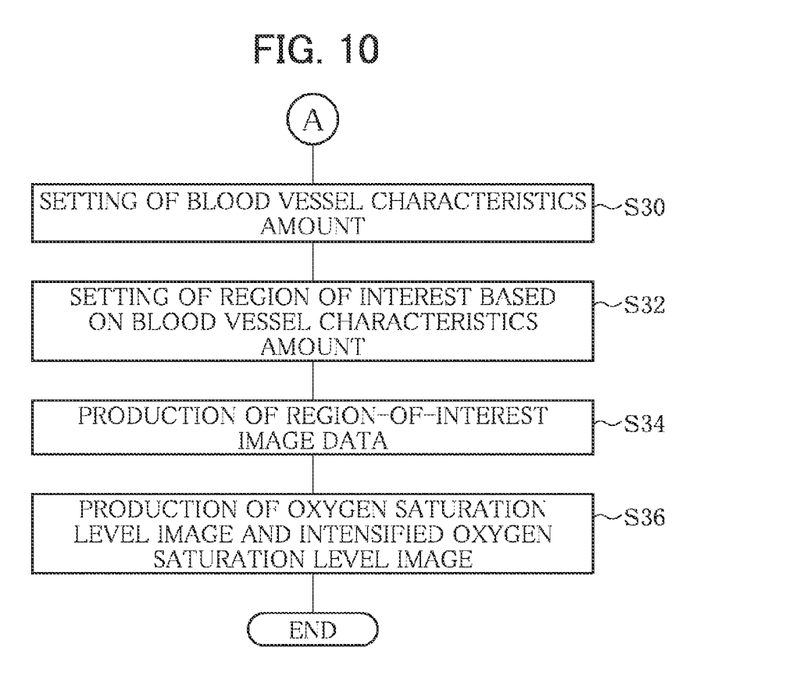
FIG. 10 is the second half of the flow chart illustrating a procedure of calculating blood vessel depth-oxygen saturation level information, a procedure of specifying a region of interest, and a procedure of producing an oxygen saturation level image and an enhanced oxygen saturation level image incorporating that information.

Next, the blood vessel characteristics amount setting means 83 sets the blood vessel characteristics amount in response to an instruction from the console.

Upon setting of the blood vessel characteristics amount, the region-of-interest setting means 84 reads out the first narrowband image data from the memory 56 and sets the region of interest based on the blood vessel characteristics amount for the first narrowband image data.

The region-of-interest setting means 84 sets a region of interest to produce the region-of-interest setting image data for displaying the region of interest enhanced in the first narrowband image. The region-of-interest setting image data thus produced is stored again in the frame memory.

Then, when the oxygen saturation level information and the color information corresponding to that information have been obtained and stored for all the pixels in the blood vessel region and the region-of-interest setting image data has been produced and stored, the oxygen saturation level image producer 64 reads out the first narrowband image data and the region-of-interest setting image data from the frame memory 56 and incorporates the color information and enhanced color saturation information stored in the RAM in the first narrowband image data and the region-of-interest setting image data to produce the oxygen saturation level image data and the intensified oxygen saturation level image data. The oxygen saturation level image data and the enhanced oxygen saturation level image data thus produced are stored again in the frame memory 56.

The display control circuit 58 reads out the first narrowband image data, the oxygen saturation level image data, and the enhanced oxygen saturation level image from the frame memory 56 and displays the first narrowband image 72, the oxygen saturation level image 73, and the enhanced oxygen saturation level image 74 as illustrated in FIG. 7 or 8 on the monitor 14 based on the read-out image data. The monitor 14 illustrated in FIG. 7 displays the enhanced oxygen saturation level image 74 and one of the first narrowband image 72 and the oxygen saturation level image 73 simultaneously in juxtaposition; the monitor 14 illustrated in FIG. 8 displays the three images, i.e., the first narrowband image 72, the oxygen saturation level image 73, and the enhanced oxygen saturation level image 74, simultaneously in juxtaposition.

As described above, the present invention, comprising both the blood vessel characteristics amount setting means and the oxygen saturation level setting means, permits display of a selectively enhanced oxygen saturation level of a characteristic blood vessel portion that is of diagnostic interest.

We have described above the first embodiment of the invention.

The electronic endoscope system according to the second embodiment of the invention is similar to the electronic endoscope system 10 according to the first embodiment except for the blood vessel characteristics amount setting means 83 and the region-of-interest setting means 84. Therefore, drawings and descriptions of the other features will not be provided below.

According to the second embodiment of the invention, the blood vessel characteristics amount setting means 83 sets a blood vessel density as the blood vessel characteristics amount in the acquired image.

According to this embodiment, where a blood vessel density is set as the blood vessel characteristics amount, the region-of-interest setting means 84 sets a region of interest based on the blood vessel density.

First, the interest region setting means 84 acquires the first narrowband image data stored in the frame memory 56, and then extracts micro blood vessels having a diameter of about 10 μm to 50 μm from the first narrowband image data. Then, the interest region setting means 84 extracts, in particular, a portion having a high blood vessel density from the blood vessel region containing the thus extracted micro-blood vessels. The extraction of the portion having a high blood vessel density is achieved by binarizing the first narrowband image where the micro-blood vessels were extracted (blood vessel extracted image). The blood vessel extracted image is binarized by assigning a pixel value of 1 to the pixels of a blood vessel in that image and a pixel value of 0 to the other pixels. A threshold value used in assignment of 1 and 0 may for example be a mean value of the pixel values of the blood vessel extracted image.

The region-of-interest setting means 84 judges whether the individual pixels in a binarized image binarized by the above method belong to a high blood vessel density region. A pixel is judged to be a high blood vessel density region when the proportion of white pixels in a given square region centering on that particular pixel is greater than a given threshold value.

Preferably, the given threshold value is for example about 30% and the size of the square is for example about a thousandth of the whole image.

Thus, a high blood vessel density region can be extracted from the first narrowband image data.

Then the image data where the high blood vessel density regions have been extracted is stored in the frame memory 56 as the region-of-interest setting image data.

The procedure to follow is the same as with the electronic endoscope system 10 according to the first embodiment.

The electronic endoscope system according to the second embodiment of the invention is similar to the electronic endoscope system 10 according to the first embodiment except for the blood vessel characteristics amount setting means 83 and the region-of-interest setting means 84. Therefore, drawings and descriptions of the other features will not be provided below.

According to the third embodiment of the invention, the blood vessel characteristics amount setting means 83 sets a blood vessel branch point density as the blood vessel characteristics amount in the acquired image.

According to this embodiment, where a blood vessel branch point density is set as the blood vessel characteristics amount, the region-of-interest setting means 84 sets a region of interest based on the blood vessel branch point density.

First, the interest region setting means 84 acquires the first narrowband image data stored in the frame memory 56, and then extracts micro-blood vessels having a diameter of about 10 μm to 50 μm from the first narrowband image data. Then, the interest region setting means 84 extracts, in particular, a portion having a high blood vessel branch point density from the blood vessel region containing the thus extracted micro-blood vessels. The extraction of the portion having a high blood vessel branch point density may be achieved by binarizing the first narrowband image where micro-blood vessels were extracted (blood vessel extracted image) as in the second embodiment to search for branch points in the binarized blood vessel extracted image by a template matching method. That is, a small V-shaped reference binarization image representing a blood vessel branch point is produced to search for points where the difference from that reference image is not greater than a given threshold value.

Because bloods bifurcate in various directions and at various angles, reference images having a plurality of patterns need to be produced. From the branch points thus extracted, a region is further extracted where branch points concentrate with a high density using the same method as in the second embodiment.

Thus, a high blood vessel branch point density region can be extracted from the first narrowband image data.

Then the image data where the high blood vessel branch point density region has been extracted is stored in the frame memory 56 as the region-of-interest setting image data.

The procedure to follow is the same as with the electronic endoscope system 10 according to the first embodiment.

The present invention is basically as described above. The present invention is not limited to any of the embodiments described above and permits various modifications to be made without departing from the spirit thereof.

I claim:

1. An electronic endoscope system comprising:
   a light source device for sequentially emitting plural kinds of light having different wavelength bands from each other;
   an electronic endoscope for sequentially illuminating the plural kinds of light emitted from said light source device to a subject tissue containing blood vessels inside a body cavity, sequentially receiving the plural kinds of reflected light of the illuminated light from the subject tissue, and sequentially outputting image data of acquired images corresponding to the plural kinds of received light having the different wavelength bands;
   a blood vessel characteristics amount setting unit configured to set as a blood vessel characteristics amount related to the blood vessel a diameter of the blood vessel from the image data of at least one of the acquired image outputted from said electronic endoscope;
   an interest region setting unit configured to set a region of interest in the acquired image by said electronic endoscope based on the blood vessel characteristics amount calculated by said blood vessel characteristics amount setting unit;
   a first image production unit configured to produce a first oxygen saturation level image representing a distribution of an oxygen saturation level in the blood vessel in simulated color from the image data of the acquired images;
   a second image production unit configured to produce a second oxygen saturation level image in which the oxygen saturation level within the region of interest set by said interest region setting unit is selectively enhanced in the first oxygen saturation level image produced by said first image production unit; and
   an image display unit configured to display in the simulated color both the first oxygen saturation level image produced by said first image production unit and the second oxygen saturation level image produced by said second image production unit,
   wherein said blood vessel characteristics amount setting unit applies a two-dimensional filter corresponding to the diameter of the blood vessel to the image data of the acquired image to extract a blood vessel having the diameter of the blood vessel, and
   wherein said interest region setting unit sets a region of the extracted blood vessel by said blood vessel characteristics amount setting unit as the region of interest.

2. The electronic endoscope system according to claim 1, wherein said interest region setting unit sets a region of the blood vessel having a given diameter as the region of interest.

3. The electronic endoscope system according to claim 2, wherein said interest region setting unit sets a region of micro blood vessel having a diameter of 10 μm to 20 μm as the region of interest.

4. The electronic endoscope system according to claim 1, wherein said second image production unit increases a color saturation of the oxygen saturation level in the simulated color within the region of interest to selectively enhance the oxygen saturation level within the region of interest in the second oxygen saturation level image.

5. The electronic endoscope system according to claim 1,
   wherein said light source device sequentially emits plural kinds of narrowband light having different wavelength bands from each other;
   wherein said electronic endoscope sequentially receives the plural kinds of reflected narrowband light of the illuminated light from the subject tissue, and sequentially outputs image data of acquired narrowband images corresponding to the plural kinds of said received narrowband light;
   wherein said blood vessel characteristics amount setting unit sets said diameter of the blood vessel from the image data of at least one of said acquired narrowband images outputted from said electronic endoscope;

wherein said interest region setting unit sets a region of interest in said acquired narrowband image by said electronic endoscope based on said diameter of the blood vessel.

6. The electronic endoscope system according to claim 1, wherein said image display unit simultaneously displays said first oxygen saturation level image and said second oxygen saturation level image.

7. The electronic endoscope system according to claim 1, wherein said light source device emits at least three kinds of light including at least two kinds of first light and at least one kind of second light as said plural kinds of light having different wavelength bands, said at least two kinds of first light having wavelength bands whereby the magnitude of light absorption reverses between oxygenated hemoglobin and reduced hemoglobin in the blood vessel depending on the oxygen saturation level, said at least one kind of second light having a wavelength band whereby the absorbance coincides.

8. The electronic endoscope system according to claim 1, wherein said light source device emits three kinds of light including two kinds of first light and one kind of second light as said plural kinds of light having different wavelength bands, said two kinds of first light having wavelength bands whereby the magnitude of light absorption reverses between oxygenated hemoglobin and reduced hemoglobin in the blood vessel depending on the oxygen saturation level, said one kind of second light having a wavelength band whereby the absorbance coincides.

9. The electronic endoscope system according to claim 8, wherein said diameter of the blood vessel is determined by using one of said two kinds of first light, and wherein said distribution of the oxygen saturation level in the blood vessel is determined by using a ratio of image data of two acquired images corresponding to the two kinds of first light, and a ratio of image data of one acquired image corresponding to the one kind of second light and image data of one of said two acquired images.

* * * * *